United States Patent [19]

Yanai et al.

[11] Patent Number: 5,455,171
[45] Date of Patent: Oct. 3, 1995

[54] FUNGUS OBTAINED BY THE FUSION OF GRIFOLA UMBELLETA AND GANODERMA LUCIDUM

[76] Inventors: Kazuo Yanai; Takeshi Yanai, both of 2988-1 Azahigashiyama, Oazakawa, Moriyama-Ku, Nagoya-Shi; Isao Yanai, 49 Aza Suginoki, Oazaobata, Moriyama-Ku, Nagoya-Shi, all of Japan

[21] Appl. No.: 151,752

[22] Filed: Nov. 15, 1993

Related U.S. Application Data

[63] Continuation-in-part of Ser. No. 958,681, Oct. 9, 1992, abandoned.

[51] Int. Cl.$^6$ .............................. C12N 1/14; A61K 37/00
[52] U.S. Cl. ...................... 435/254.1; 435/911; 424/93.2; 424/93.5
[58] Field of Search .................. 435/254.1, 911; 424/93 A, 93 C, 93 Q, 93.1, 93.3, 93.5, 93.2

[56] References Cited

U.S. PATENT DOCUMENTS 5,123,203  6/1992  Hiromoto .................................. 47/1.1

*Primary Examiner*—Marian C. Knode
*Assistant Examiner*—Kristin K. Larson
*Attorney, Agent, or Firm*—Birch, Stewart, Kolasch & Birch

[57] ABSTRACT

A microorganism exhibiting excellent antibiotic and sterilizing properties for the preparation of medicines and the like, obtained by fusion of cells of two different fungal species. A Ganoderma and a Grifola, each exhibiting little or no antibiotic activity, are isolated and hybridized, and milled to produce a fused cell body. The cell body is black-brown, and has been deposited as deposit No. 3131 (FERM BP-3131).

1 Claim, 1 Drawing Sheet

FUNGUS OBTAINED BY THE FUSION OF GRIFOLA UMBELLETA AND GANODERMA LUCIDUM

This application is a continuation-in-part of application Ser. No. 07/958,681 filed on Oct. 9, 1992, the entire contents of which are hereby incorporated by reference. Application Ser. No. 07/958,681 has been abandoned.

BACKGROUND OF THE INVENTION

1. Field of the Invention

The present invention relates to a new microorganism useful for preparing medicines.

2. Description of Related Art

Recently, fusion of cells, including those of basidiomycetes, has been accomplished.

However, the frequency of reproducibility is low, and is no more than $10^{-5}$ to $10^{-7}$ (i.e., is almost impossible).

Furthermore, nuclear combination in cell fusions between different species and genera is also low.

SUMMARY OF THE PRESENT INVENTION

Nevertheless, via cell fusion of basidiomycetes, the present applicants have obtained a cell-body exhibiting special biochemical properties in a hetero-fungus by fusion of two species producing medicinal components.

DETAILED DESCRIPTION OF THE INVENTION

Figure 1:
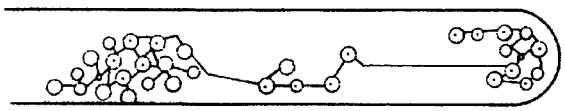
FIG. 1 shows the shape of a colony on an agar culture medium separated and germinated from the nucleus of a Grifola fungus under the microscope.

The present invention relates to a new microorganism obtained by fusing cells of fungi belonging to the genera Ganoderma and Grifola.

The new microorganism of the present invention, and the mycological properties of the Ganoderma and Grifola species utilized to form said microorganism of the present invention, are described in detail as follows:

MYCOLOGICAL PROPERTIES OF THE GANODERMA

The instant Ganoderma is *Ganoderma lucidum*.

1) Morphology

This is a mushroom that has a pileus and a stem that is lustrous, as though varnished with lacquer (when steamed). The pileus is a kidney type. Its surface is covered with a shell. Its color is a reddish brown and/or a black violet. Its pulp is corky, and consists of two layers. The upper layer is white. The portion near the spores is light cinnamon color, and the layer length of the tube is 5–10 mm. The tube hole is round, and there are 3 to 4 1 mm holes. The spore is an egg type; its membrane is dual in structure, the outer membrane being nearly colorless, the inner membrane having a weak brown small projection. Said projection is inserted from the inside to the outside. Its dimension is 9 to 11×5.5×7μ. Said shell wraps the pileus, and the stem has a thickness of 30–40μ. A brown cell of a thick club type membrane is arranged on said shell. A varnish-like material is secreted thereon.

2) Separation and Cultivation

Yellow tissue is picked from the ripe tip of the Ganoderma fruiting body, sterilely cut to a size of 3 mm$^3$, inoculated onto an onion, soy sauce, and sesame oil agar culture medium, and cultured at a temperature of 25° C. to 30° C. for germination, resulting in propagation of the first white cotton wool hypha within 7 days. Such germinated hyphae are utilized in fusions with other fungi.

Said fungus can also be propagated on culture media of any composition.

3) Oxygen requirement

Hyphae on agar culture media generate only a small quantity of $CO_2$, require a very small amount of $O_2$, and are aerobic. Since $CO_2$ is generated in large quantities during propagation and cultivation on sawdust, when fruiting bodies are generated, a large amount of $O_2$ is required. Thus, sufficient ventilation is necessary.

4) Growth temperature

The growth temperature is in the range of 5° C. to 30° C., but it differs depending upon the mycetoma, and the optimum temperature is 30° C.

Hyphae can also be grown continuously at 5° C.

5) Growth pH

The growth pH is neutral, as weak alkali and $CaCO_3$ are necessary. At a pH of 7.0 to 8.5, growth on agar culture media is retarded.

6) Antibiotic activity

When a fruiting body is wetted and air is blown thereon, adhesion of molds in the air is excellent in basidiomycetes. When an extract of said fruiting body is allowed to stand, it becomes a good nutrient for molds in the air. Propagation of the molds is good; however, they do not have antibiotic activity.

7) The taste

A water solution of the Ganoderma has an intensive bitter taste.

8) Utilization in Chinese (herb) medicine

In China, Ganoderma is a spirit grass, and is a folk remedy medicine i.e., a hermit medicine, disclosed in "A Shinnong Boncho Kyeong," meaning a hermit agricultural botanical bible.

MYCOLOGICAL PROPERTIES OF THE GRIFOLA

Grifola, as used herein, means the sclerotium in soil of *Grifola umbellata*. Those utilized for fusion in the present invention are cell bodies of germinated Grifola.

1) Morphology

A sclerotium body produced in Japan is referred to as "Chinjeoryeong", meaning a true Grifola. Its flesh is thin and irregular. A sclerotium body produced in China has thick flesh. In herb medicine, Chinese products are recognized as important medicines.

A fruiting body produced above ground is an annual plant. It is branched from one plant similar to a bush clover mushroom. It is 10–25 cm tall, and its soil sclerotium is a glass bead type or is flat. It is connected in the form of a ginger root, its surface is black or gray-black, and the inner flesh is white and rich.

2) Separation and Cultivation

The inner tissue of *Grifola umbellata* is cut to a size of 3 mm$^3$. This is inoculated onto a sterile nutrient culture medium containing a boiling water extract of Grifola. It is cultured at 25°–30° C. to produce mycelia.

3) Requirement for $O_2$

It is aerobic.

4) Growth temperature

20°–28° C. Optimum temperature is 22° C. Below 5° C., growth is stopped.

5) Growth pH pH 6.0–7.0

6) Antibiotic activity

When a dried sclerotium was stored wet, adhesion and germination of molds were not observed for a year.

Further, when an extracted concentrate thereof is heated at 30° C. in an unsterilized state and then stored, antibiotic activity thereof was not observed.

7) Utilization in herb medicine

Referring to the action of Grifola in herb medicine, when 5 g of decocted Grifola is administered to a healthy human, after 6 hours the quantity of urine is increased 62%, and chloride in the urine is increased 45%.

However, 3 g of a decoction of Grifola causes no diuresis.

In an experiment involving a dog having urenia, when 0.25–0.5 g/kg of a decoction of a Grifola is administered by intravenous or intramuscular injection, the diuretic activity thereof is observed; however, by oral or intravenous injection of no more than 0.0048 g/kg of a decoction of Grifola, said activity was not observed.

In toxicity testing in a rabbit, until a dosage for humans by oral or intraperitoneal injection is administered thereto, no effect was observed.

When a water solution of an extract of Grifola extracted with alcohol is administered orally to a mouse, the quantity of urine is increased.

However, in the case of a mouse in which the adrenal bodies are removed, although a decoction of a Grifola and deoxycorticosterone are administered together, the quantity of secretion of urine and chloride from it is unchanged.

An alcohol extract of the Grifola is inhibitory against a yellow *Staphylococcus* and *Escherichia coli*, and a water soluble glucan obtained from the Grifola exhibits intensive antitumor activity in a mouse suffering from bladder cancer.

Method for Producing the Present Fusion Fungus—Fusion of Mycelia of *Ganoderma lucidum* and *Grifola umbellata*

Mountain soil from a mushroom-growing district is dried, sifted using a 100 mesh sieve to produce microparticles of soil, and the resulting sieved 100 mesh soil is dried and sterilized at 150° C. for two hours to obtain microparticles of soil having a pH of 4.5–5.0. To said obtained soil a 40% aqueous solution of PEG is added with agitation, and the mixture is sterilized in an autoclave at 120° C. for 1.5 hours to give a sterilized, agitated soil-PEG mixture.

A very small amount of the resulting mixture is added to a mixture of mycelia of *Ganoderma lucidum* and *Grifola umbellata* in a mortar. This is crushed together, and is inoculated on the surface of agar medium for a mushroom and is placed in a transparent airtight pouch equipped with a stopper.

The mouth of said pouch is bottled up by electrical melt adhesion. The inside of said pouch is evacuated, and $CO_2$ gas is injected into said pouch. The mixture in said pouch is cultured for 30–40 days to produce dark brown mycelia wherein mycelia of *Ganoderma lucidum* and *Grifola umbellata* are fused.

Propagation of Said Fused Mycelia on Sawdust Medium

A mixture of 70% sawdust of a broadleaved tree and 30% bran are mixed with water while stirring, and is placed in a heat-resistant glass bottle or tube. This is sterilized under 1.2 kg/cm$^2$ of pressure at 120° C. for two hours, and is cooled. Said fused mycelia are inoculated on the surface of said treated mixture of sawdust and bran placed in the bottle. Said inoculated bottle is placed in a pouch which consists of a polypropylene film layer and a polypropylene nonwoven layer having micropores of 0.5–02.μ to provide sterile air. Then the mouth of said pouch is bottled up by electrical melt adhesion and culturing is carried out at 25° C. for 120 days to propagate black-brown mycelia.

Mycological Properties of the Present Fused Fungus

1) Growth pH of the Fused Fungus

A black-brown fungus is generated in the range of pH 4.5–5.0.

2) $O_2$ Requirement of the Fused Fungus

Since it is propagated in sawdust medium, sufficient $O_2$ should be provided.

3) Antibiotic Activity

Ganoderma or Grifola alone do not exhibit antibiotic activity. However the fused fungus exhibits intensive antibiotic activity.

4) Bactericidal Action

When an extract of the fused fungus is employed to treat cutaneous disease, athlete's foot, purulent matter of the gums, eczema, and dermatophytosis, it is highly effective.

Difference in Properties Between Ganoderma, Grifola, and the Present Fused Fungus 1) Sclerotium of Grifola Colonies on an agar culture medium separated and germinated from a sclerotium of a Grifola are black-brown or black, and are globular in shape. They are no more than ¼–⅛ the size of a black sesame oil seed, and are connected by invisible microhyphae.

The connected globular fungus grows in a piled state (tumor-like), while the hyphae are extended on the agar surface. When it grows against the glass wall of a test tube, since its extension is controlled, its tip is inflated to form a globular mass.

Its shape is shown in FIG. 1 as observed microscopically or visibly.

The cell body is an aggregate of globular masses.

When the pH of the culture medium is 4–5.5, its growth is stopped.

2) Ganoderma Fungus

Referring to the properties and shape of hyphae of Ganoderma on an agar surface, it grows in the form of white cotton wool. When the Ganoderma fungus has aged, adhesion of other saprophytic bacteria is great, and thereby the Ganoderma fungus withers and dies.

A water extract from the cell body of Ganoderma has nutrient properties for saprophytic bacteria, and it does not exhibit antibiotic activity.

It grows well on an onion, soy sauce, and sesame oil agar culture medium.

Figure 2:
FIG. 2 shows the shape of a Ganoderma hypha under the microscope.
Figure 5:
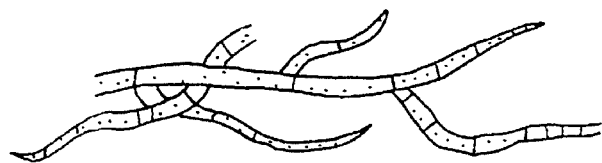
FIG. 5 shows the shape observed during the adolescent growth stage of the fusion fungus under the microscope.
Figure 3:
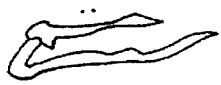
FIG. 3 shows the shape of a fusion fungus of the present invention under the microscope, grown on an onion, soy sauce and sesame oil agar culture medium.

The shape of the Ganoderma hypha is as shown microscopically in FIG. 2, wherein each hypha has alternate projections on it.

3) Properties and Identification of the Present Fused Fungus (a) It does not entirely adhere or germinate on other saprophytes and the like (opened and cultivated in air), and it has intensive bactericidal action.

(b) The black-brown fungus adheres to and grows on sawdust propagation medium.

(c) It grows well on an onion, soy sauce, and sesame oil agar culture medium (pH 6.0–6.5). It grows as an aggregation of mixed white hyphae and black-brown hyphae, and does not have projections.

Figure 4:
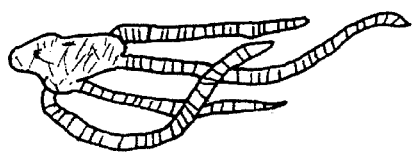
FIG. 4 shows the shape observed for the early stage of growth of the fusion fungus under the microscope on a YM-12 flat agar culture medium.

(d) The hyphae on YM-12 agar culture medium are disposed with equally spaced black lines (FIG. 4).

It is observed that said fungus becomes black-green due to the pH of YM-12 medium.

(e) The morphology and properties of the present fused fungus are not found in the literature.

Test for Antibiotic Activity of Water Extracts of Each Fungus, (Ganoderma, Grifola, and the present Fused Fungus)

In a test of the antibiotic activity of Ganoderma, many species of molds are generated on an extract of the Ganoderma.

In a test of an extract of a sclerotium of Grifola, there is little antibiotic activity.

A water extract of the sawdust propagation medium used to cultivate the fused fungus is colorless and transparent, and exhibits intensive antibiotic activity.

Summary of the Properties of the Present Fused Fungus

The color of the present fused fungus propagated on sawdust is black-brown.

Its water extract exhibits intensive antibiotic activity. In contrast, the water extract of basidiomycetes is a good nutrient source for molds and the like (cultivation at 32° C. for seven days).

The cell body of Grifola on agar culture media is a globular aggregate, and it has spheroid masses on the outer surface.

Accordingly, it will be appreciated that this is entirely different from the present fused fungus.

Toxicity of the Fused Mycelia ($G^2 \cdot sY$)

A toxicity test of the fused mycelia was carried out as follows:

BALB/C($\delta$) Mouse Experimental Process

A mixture of 100 g of the fusion mycelia propagated on sawdust medium and pure water is poured in a container, boiled, concentrated to a volume of 300 ml, filtered using conventional filter paper to give a flitrate, and then is filtered again using a 0.2 μm filter. Minute particles in the resulting filtrate are removed by centrifugation at 5000 rpm/20 min. The supernatant is sterilized in an autoclave under a pressure of 1.2 kg/cm$^2$ at 120° C. to produce a solution for intravenous injection.

0.2 ml of solution was administered to a mouse, but the mouse no showed physical reaction.

In a test employing rabbits, when 20 ml of solution is injected intravenously into the ear of a Japanese white female rabbit, the rabbits showed no physical reaction.

These results demonstrate that the fusion mycelia causes no physical toxicity at these levels.

Oral Administration Test in Humans

When the fusion mycelia is administered to 200 gastric ulcer patients, all patients were completely cured before or after 10 days.

The method for oral administration of the fusion mycelia to humans is as follows:

1 kg of raw fusion mycelia are extracted with water, concentrated to a volume of 6 liters, and then the resulting extracted solution is administered to the subject 20 ml at a time, ter in die (three times a day), one hour before meals.

Effect on Cancer Patients

The aches of a cancer patient are gone after 3–5 days by administration of 1–2 liters of the fusion mycelia extract.

Utility of the Present Invention

The fused microorganism of the present invention has antibiotic properties, and can be utilized for the preparation of medicines and the like.

Deposit

The present fusion fungus $G^2 \cdot sY$ was deposited under the terms of the Budapest Treaty as accession number FERM BP-3131 on Oct. 12, 1990, at the Fermentation Research Institute, Agency of Industrial Science and Technology, 1-3, Higashi 1 chome, Tsukubashi, Ibaraki-ken, 305, Japan.

What is claimed is:

1. A strain of a black-brown fungus obtained by the fusion of *Grifola umbellata* and *Ganoderma lucidum*, said strain having all the identifying characteristics of $G^2$-sY.

\* \* \* \* \*